(12) United States Patent
Batchelor et al.

(10) Patent No.: US 11,547,435 B2
(45) Date of Patent: *Jan. 10, 2023

(54) COOLED BURR SURGICAL INSTRUMENTS

(71) Applicant: GYRUS ACMI, INC., Southborough, MA (US)

(72) Inventors: Kester Julian Batchelor, Mound, MN (US); Jeffrey J. Nelson, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 346 days.

This patent is subject to a terminal disclaimer.

(21) Appl. No.: 16/869,098

(22) Filed: May 7, 2020

(65) Prior Publication Data

US 2020/0289151 A1    Sep. 17, 2020

Related U.S. Application Data

(60) Continuation of application No. 15/872,218, filed on Jan. 16, 2018, now Pat. No. 10,675,054, which is a
(Continued)

(51) Int. Cl.
*A61B 17/3207* (2006.01)
*A61B 17/32* (2006.01)
(Continued)

(52) U.S. Cl.
CPC ........ *A61B 17/320758* (2013.01); *A61B 17/32002* (2013.01); *A61B 2017/00973* (2013.01);
(Continued)

(58) Field of Classification Search
CPC ...... A61B 17/320758; A61B 17/32002; A61B 2017/00973; A61B 2018/00005; A61B 2217/005; A61B 2217/007
See application file for complete search history.

(56) References Cited

U.S. PATENT DOCUMENTS

| 4,411,266 A | 10/1983 | Cosman |
| 5,030,201 A | 7/1991 | Palestrant |

(Continued)

OTHER PUBLICATIONS

"U.S. Appl. No. 14/624,070, Examiner Interview Summary dated Jun. 20, 2017", 3 pgs.
(Continued)

*Primary Examiner* — Phong Son H Dang
(74) *Attorney, Agent, or Firm* — Schwegman Lundberg & Woessner, P.A.

(57) ABSTRACT

Featured is a surgical instrument including an end effector such as a rotating cutting implement and a heat transfer mechanism such as a cooling device, such as can include a phase change device, such as can be configured to absorb heat energy during the use of such a rotating cutting implement. The heat transfer mechanism can be configured so the absorbed heat energy is communicated to an external heat sink. Such a heat transfer mechanism can include a heat pipe, e.g., a scintered or wick type heat pipe. The heat energy is absorbed at one end of the heat pipe to minimize the potential for damage to the tissue and the like at and/or about the surgical site. Also featured are a surgical apparatus embodying such a surgical instrument and surgical or medical methods or procedures for manipulating, rotatably cutting, grinding, abrading or debriding tissue, bone or other structures or components of a mammalian body using such surgical instruments or surgical apparatus.

10 Claims, 7 Drawing Sheets

Related U.S. Application Data division of application No. 14/624,070, filed on Feb. 17, 2015, now Pat. No. 9,901,364.

(60) Provisional application No. 61/942,192, filed on Feb. 20, 2014.

(51) Int. Cl.
*A61B 17/00* (2006.01)
*A61B 18/00* (2006.01)

(52) U.S. Cl.
CPC ............ *A61B 2018/00005* (2013.01); *A61B 2217/005* (2013.01); *A61B 2217/007* (2013.01)

(56) References Cited

U.S. PATENT DOCUMENTS

| | | | |
|---|---|---|---|
| 5,190,539 A | | 3/1993 | Fletcher et al. |
| 5,403,318 A | | 4/1995 | Boehringer et al. |
| 5,417,686 A | | 5/1995 | Peterson et al. |
| 5,647,871 A | * | 7/1997 | Levine ............ A61B 18/1442 606/49 |
| 5,951,546 A | | 9/1999 | Lorentzen |
| 6,099,524 A | | 8/2000 | Lipson et al. |
| 6,575,969 B1 | | 6/2003 | Rittman, III et al. |
| 6,701,173 B2 | | 3/2004 | Nowinski et al. |
| 6,719,723 B2 | | 4/2004 | Werneth |
| 6,733,501 B2 | * | 5/2004 | Levine ............ A61B 18/1402 606/49 |
| 6,736,837 B2 | | 5/2004 | Fox |
| 7,488,322 B2 | | 2/2009 | Brunnett et al. |
| 7,879,037 B2 | | 2/2011 | Brunnett et al. |
| 7,998,159 B2 | | 8/2011 | Edwards |
| 8,150,499 B2 | | 4/2012 | Gelbart et al. |
| 8,414,580 B2 | | 4/2013 | Rioux et al. |
| 8,491,585 B2 | | 7/2013 | Hannani et al. |
| 9,179,968 B2 | | 11/2015 | Leo et al. |
| 9,717,520 B2 | | 8/2017 | Zeroni et al. |
| 9,901,364 B2 | | 2/2018 | Batchelor et al. |
| 10,675,054 B2 | | 6/2020 | Batchelor et al. |
| 2002/0019644 A1 | | 2/2002 | Hastings et al. |
| 2003/0055404 A1 | | 3/2003 | Moutafis |
| 2005/0054972 A1 | | 3/2005 | Adams et al. |
| 2005/0203505 A1 | | 9/2005 | Megerman et al. |
| 2005/0261692 A1 | | 11/2005 | Carrison et al. |
| 2006/0004369 A1 | | 1/2006 | Patel et al. |
| 2007/0073285 A1 | * | 3/2007 | Peterson ............ A61B 18/1477 606/41 |
| 2009/0149848 A1 | | 6/2009 | Werneth et al. |
| 2009/0254083 A1 | * | 10/2009 | Wallace ............ A61B 18/1482 606/41 |
| 2009/0270894 A1 | * | 10/2009 | Rubin ............ A61M 1/842 600/156 |
| 2010/0286695 A1 | | 11/2010 | Hannani et al. |
| 2013/0090650 A1 | | 4/2013 | Jenson et al. |
| 2013/0172919 A1 | | 7/2013 | Carrison |
| 2015/0230821 A1 | | 8/2015 | Batchelor et al. |
| 2015/0351836 A1 | | 12/2015 | Prutchi |
| 2016/0053653 A1 | | 2/2016 | Han et al. |
| 2016/0287278 A1 | | 10/2016 | Stigall et al. |
| 2018/0132889 A1 | | 5/2018 | Batchelor et al. |

OTHER PUBLICATIONS

"U.S. Appl. No. 14/624,070, Non Final Office Action dated Mar. 15, 2017", 12 pgs.

"U.S. Appl. No. 14/624,070, Notice of Allowance dated Oct. 24, 2017", 11 pgs.

"U.S. Appl. No. 14/624,070, Response filed Jan. 19, 2017 to Restriction Requirement dated Dec. 15, 2016", 2 pgs.

"U.S. Appl. No. 14/624,070, Response filed Jun. 15, 2017 to Non Final Office Action dated Mar. 15, 2017", 16 pgs.

"U.S. Appl. No. 14/624,070, Restriction Requirement dated Dec. 15, 2016", 9 pgs.

"U.S. Appl. No. 15/872,218, Non Final Office Action dated Sep. 19, 2019", 9 pgs.

"U.S. Appl. No. 15/872,218, Notice of Allowance dated Jan. 30, 2020", 11 pgs.

"U.S. Appl. No. 15/872,218, Preliminary Amendment filed Jan. 16, 2018", 8 pgs.

"U.S. Appl. No. 15/872,218, Response filed Dec. 13, 2019 to Non Final Office Action dated Sep. 19, 2019", 8 pgs.

"Heat Pipe", Wikipedia, the free encyclopedia, (Oct. 20, 2013), 4 pgs.

"Heat Pipes and its applications", Project Report, 2008MVK160 Heat and Mass Transport, Department of Energy Sciences, Faculty of Engineering, Lund University, (May 7, 2008).

U.S. Appl. No. 14/624,070 U.S. Pat. No. 9,901,364, filed Feb. 17, 2015, Heat Pipe Cooled Burr Including Surgical Instruments Embodying Same.

U.S. Appl. No. 15/872,218 U.S. Pat. No. 10,675,054, filed Jan. 16, 2018, Heat Pipe Cooled Burr Including Surgical Instruments Embodying Same.

\* cited by examiner

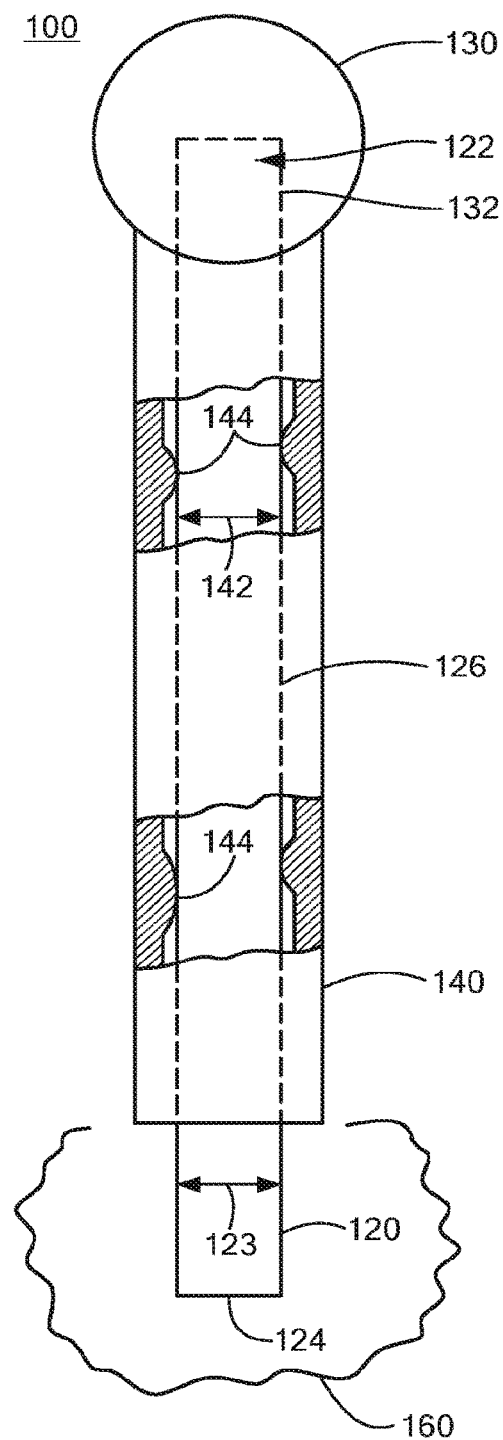
FIG. 1
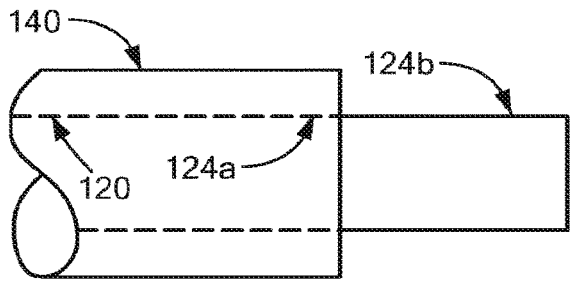
FIG. 1A
FIG. 1B

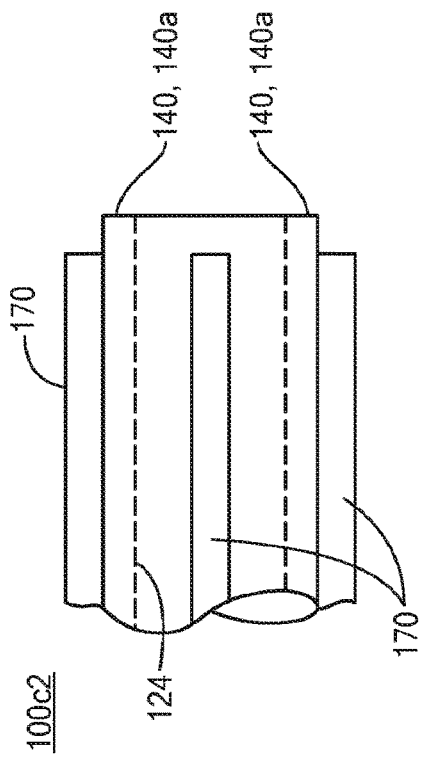
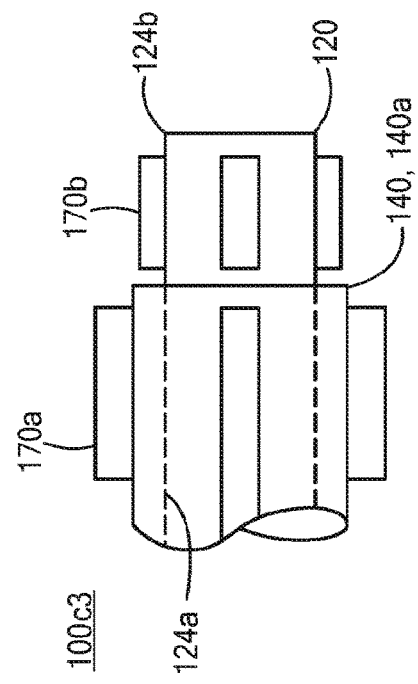
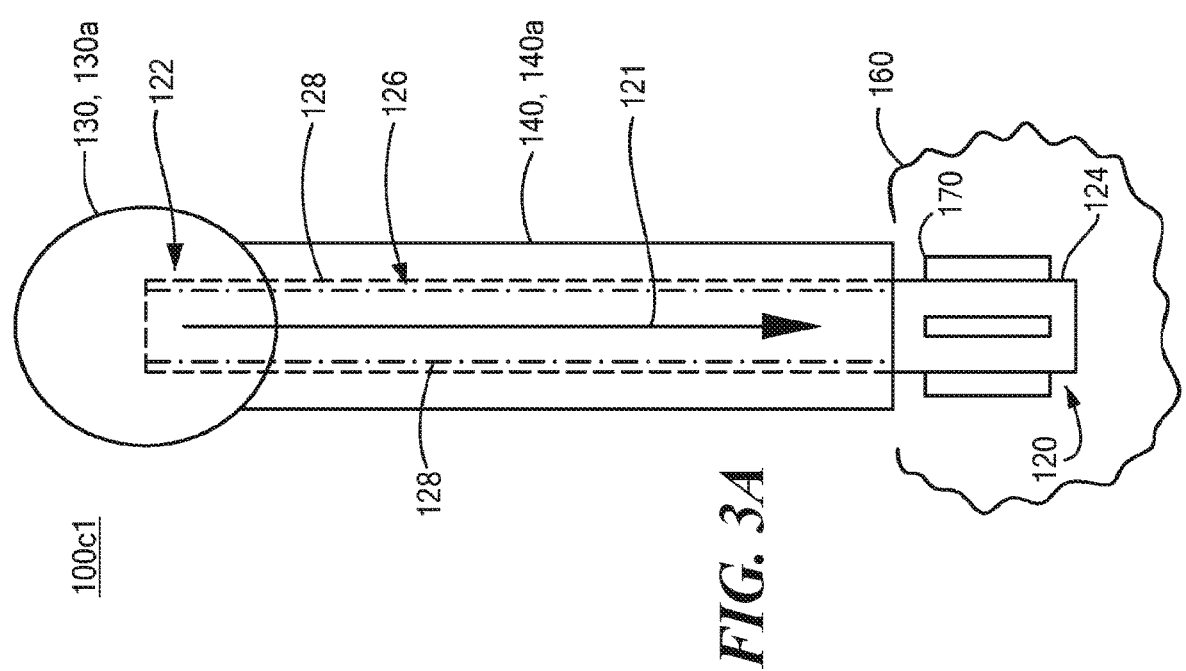

COOLED BURR SURGICAL INSTRUMENTS

CROSS-REFERENCE TO RELATED APPLICATIONS

This application is a continuation of U.S. patent application Ser. No. 15/872,218, filed on Jan. 16, 2018, which is a division of U.S. application Ser. No. 14/624,070, filed Feb. 17, 2015 and issued on Feb. 27, 2018 as U.S. Pat. No. 9,901,364, which application claims the benefit of U.S. Provisional Application Ser. No. 61/942,192 filed Feb. 20, 2014, the teachings of all of which are incorporated herein by reference in their entireties.

FIELD OF INVENTION

The present invention generally relates to surgical instruments, more particularly to powered surgical instruments that are configured to cut, abrade or the like tissue during a surgical procedure such as an ENT procedure, and even more particularly to powered surgical instruments that are configured to cut, abrade or the like tissue and also configured to minimize tissue damage (e.g., collateral tissue damage) from heating during such operation of the surgical instrument. The present invention also relates to surgical apparatus as well as methods that embody such surgical instruments or related techniques.

BACKGROUND OF THE INVENTION

There are surgical apparatus (e.g., powered surgical apparatus) that are configured so as to enhance shaving, cutting and/or removal of tissue, bone and/or other bodily material. Such surgical apparatus can include a shaving or cutting instrument, such as a rotating blade or a rotating burr for example. The rotating cutting implement also is connected to a hand piece which is held by an operator of the apparatus, such as a surgeon, for example. The surgeon, by holding the hand piece in their hand, can manipulate the rotating cutting implement to grind, shave or cut desired tissue, bone and/or other bodily material.

However, tissue abrading burrs used in connection with conventional surgical procedures can cause heating of the tissue being reduced or abraded. Such heating becomes an issue or concern when the heating begins to modify the tissue being reduced through the temperature rise attributable to the rotating burr or cutting element rather than through the intended mechanical abrasion. Such heating also can cause heating of the surrounding tissue thereby also leading to collateral tissue being damaged. For example, devices embodying such rotating burrs in connection with ear, nose and throat (ENT) surgical procedures can lead to collateral tissue damage as well as accidental tissue damage during extraction.

One conventional technique used to limit the effects of heating while using a rotating surgical cutting instrument (e.g., when grinding, reducing or modifying tissue, bone or teeth in a human body) involves irrigation of the surgical site with a fluid or liquid such as water or saline solution. In this technique, the fluid (e.g., water or saline) solution is actively dispersed (e.g., pumped, sprayed) at the surgical site and suction is concurrently applied to remove the fluid as well as any debris (e.g., tissue, bone, etc.) that is contained in the fluid. In this way, the fluid being dispersed can absorb the heat energy and the thus heated fluid is removed by suction.

In further embodiments, the surgical instrument can be configured so it disperses or suctions the fluid and/or a separate device(s) can be provided to disperse and suction the fluid. Such techniques, however, may not be suitable for all surgical procedures or introduce added complexities because the introduction of a fluid at a given site in a sufficient quantity to control temperature rise may not be optimal.

Referring now to U.S. Pat. No. 6,733,501 there is found an electrosurgical device having electrodes to cauterize, cut and/or coagulate tissues. In such a device. RF energy or the like is applied to the tissues using one or more electrodes to achieve the desired surgical effect. However, such cutting or cauterizing of the tissue also can cause less than optimal initial conditions for the procedure. The described electrosurgical device is configured with a heat pipe that conducts heat from the electrode where substantially all of the heat conducted from the electrode through the heat pipe is dissipated along the length of the heat pipe.

Such a heat pipe includes an internal cavity which is sealed at both ends. The cavity is partially evacuated and contains a heat transfer fluid such as water. The outer shell can be made of a conductive metallic material such as copper. The shell can be covered over most of its length by an electrically insulating cover or sheath. The exposed distal end of the heat pipe is coated with a conductive non-toxic material such as gold or nickel, for example, which forms an outer surface.

Referring now to U.S. Pat. No. 6,736,837 there is found a method for inducing hypothermia for treating neurological disorders, more particularly the invention relates generally to methods of treating cancer and other diseases by modulating body temperature. In this regard, body temperature may be directly modulated by a heat-exchange catheter positioned within a blood vessel of a patient. Such methods generally relate to methods of treating cancer by inducing hypothermia. In this technique, heat is directed to the hypothalamus, while optionally maintaining cancerous tissue at or near to normal body temperature, and optionally applying another cancer treatment. This other cancer treatment may be radiation therapy, chemotherapy, a combination of radiation and chemotherapy, or some other cancer treatment. The invention relates generally to methods of treating diseases including cancer, viral infections, and other diseases, comprising inducing hyperthermia by cooling the hypothalamus, and optionally applying another treatment, for example radiation, chemotherapy, antiviral therapy, or a combination of therapies.

Another such apparatus effective to cool a nasal passage or sinus comprises an electrical cooling device attached at an end of a flexible tube, rod or catheter capable of being introduced into the nasal passage or sinus. Such an electrical cooling device may be a Peltier device or other electrical cooling element. The Peltier device may be located at the tip of the cooling device or may be located distal to the tip and heat withdrawn from the tip by the cooling device via a heat pipe. The tip of the probe may be cooled via a heat pipe that connects the tip of the probe to a cooling element such as the Peltier device. It also is noted therein that heat pipes are described, for example, in U.S. Pat. No. 5,190,539 to Fletcher et al. and U.S. Pat. No. 5,417,686 to Peterson et al.

Referring now to U.S. Pat. No. 7,998,159 there is found an irrigated cutting device for use with a powered surgical tool. Such a device includes an elongated outer tube with an outer hub attached to the proximal end for releasably securing the cutting accessory/device within the powered tool. An elongated inner member is received within the outer tube and has an inner hub adapted to be driven by the surgical tool. The dimensions of the outer tube and inner member are such as to form an annular channel there between for the passage of irrigating fluid. The inner member carries a cutting tool, such as a burr, at its distal end, the tool being accessible through an aperture in the outer tube. A bypass channel runs external to the outer tube to carry irrigating fluid to the cutting tool. An aperture through the outer tube connects the annular channel with the bypass channel.

The fluid passes through the aperture into the external bypass tube, and along the bypass tube before exiting adjacent the burr. In this way, the irrigating fluid is directed on to the burr, to provide the maximum cooling and irrigating effect. Excess fluid, as well as tissue and bone fragments cut by the burr, pass through the suction aperture into the interior of the hollow member, and travel back up the cutting blade under the action of the suction source.

Referring now to U.S. Pat. No. 8,491,585, there is found methods and systems for minimally invasive lateral decompression of one or more spinal nerves. Such a system for laterally decompressing includes an access sheath, a tool guide, and a bone removal tool. The bone removal tool is used to remove bone from the anterior surface. Optionally, after bone removal has been completed, the cutting tool may be advanced through the access sheath in order to partially cut the ligamentum flavum to further relieve compression of the spinal nerve(s). Usually, a cooling and/or flushing medium will be introduced to the rotating burr in order to remove heat and optionally permit aspiration of the removed bone material.

Referring now to U.S. Publication No. US2013/01729191 there is found a tissue removal kit or assembly that includes a cannula and a tissue removal probe axially slidable within the cannula. The tissue removal probe includes an elongated member having a distal end configured to curve when distally deployed from the cannula. The tissue removal probe further comprises a drive shaft and a rotatable tissue removal element (e.g., an abrasive burr) disposed on the drive shaft adjacent the member distal end. The curved member distal end may associate the tissue removal element, which has its own axis of rotation, with a radius of revolution about the longitudinal axis of the member. The member is laterally flexible and resilient, so that the radius of revolution can be adjusted. In this manner, the tissue removal element can remove tissue around an adjustable arc. An irrigation fluid is provided to help cool the drive shaft and/or the burr, while the burr is rotating at high speed and grinding against tissue. The media or fluid also washes away debris at the target site.

It thus would be desirable to provide a surgical instrument having a cutting or abrading cutting element such as a burr that embodies a mechanism for directly cooling the cutting element or burr to minimize temperature rise in surrounding tissue as well as methods related thereto. It would be particularly desirable to provide such a surgical instrument, surgical apparatus and method that would minimize temperature rise when using the surgical instrument in comparison to prior art devices, apparatus and methods.

SUMMARY OF THE INVENTION

The present document features a surgical instrument and a surgical apparatus embodying such a surgical instrument. The surgical instrument can include a heat transfer mechanism, such as a cooling device, such as can include a phase change device, such as can be configured to absorb heat energy being developed such as during use of an end effector such as a rotating cutting implement. Such a heat transfer mechanism also is configured so that the absorbed heat energy is communicated to a heat sink that is remote from the surgical site. In this way, the absorbed heat energy is removed so as to minimize the potential for damage to the tissue and the like at and/or about the surgical site. Also featured are surgical or medical methods or procedures for manipulating, rotatably cutting, grinding, abrading or debriding tissue, bone or other structures or components of a mammalian body using such surgical instruments or motorized/powered surgical apparatus.

In more particular aspects the present invention features a surgical instrument that includes a rotating cutting implement for use in processing a part of a mammalian body and a heat pipe that is arranged so as to absorb heat energy at one end thereof and to dissipate the heat energy at least at a second end thereof. In addition, the rotating cutting implement and heat pipe are arranged so that the heat pipe first end is thermally coupled to the rotating cutting implement so that at least some heat energy being developed by the rotating cutting implement during use is absorbed by the heat pipe first end and is communicated in the direction of the heat pipe second end.

According to another aspect of the present invention there is featured a surgical instrument having a rotating cutting element, where the cutting element comprises a burr having a given shape. Such a surgical instrument also includes a heat pipe. In addition, the burr and heat pipe are arranged so that the heat pipe first end is thermally coupled to the burr such that at least some heat energy being developed by the burr implement when in use is absorbed by the heat pipe first end and is communicated in the direction of the heat pipe second end. Also included is a tubular member that is connected to the burr and extends outwardly from the burr such that a longitudinal extending portion of the heat pipe is disposed within the tubular member and wherein the burr includes a cavity that is configured and arranged to receive at least a portion of the heat pipe first end therein.

In embodiments of such surgical instruments, the heat pipe further includes a material disposed in the interior of the heat pipe to facilitate movement of a phase change medium along a length of the heat pipe. Such a material is sometimes referred to as a phase change material. In further embodiments, the phase change material is used alone or in combination with a wick type of material that facilitates movement of the phase change material (e.g., the liquid phase).

In yet further embodiments, the rotating cutting implement includes a cavity that is configured and arranged to receive at least a portion of the heat pipe first end. When so received, the heat pipe first end is at least thus thermally coupled to the rotating cutting element and preferably also is mechanically coupled to the rotating cutting element.

In further embodiments, such a surgical instrument further includes a thermally conductive medium, the thermally conductive medium being disposed in the rotating cutting implement cavity about the heat pipe first end so as to facilitate thermal coupling between the rotating cutting implement and the heat pipe first end. Such a thermal coupling medium also preferably mechanically couples the rotating cutting implement and the heat pipe.

In yet further embodiments, such a surgical instrument further includes a tubular member that is connected to the rotating cutting implement and extends outwardly from the rotating cutting implement such that a longitudinal extending portion of the heat pipe is disposed within the tubular member. Such a tubular member can further include one or more or a plurality of reduced diameter regions disposed along a length of the tubular member, each of the reduced diameter regions being formed so as to at least reduce a gap between an inner surface of the tubular member and an outer surface of the longitudinally extending portion of the heat pipe.

In yet further embodiments, the tubular member for such a surgical instrument further includes one or more or a plurality of contact regions disposed along a length of the tubular member, each of the contact regions being formed so an inner surface of the tubular member and an outer surface of the longitudinally extending portion of the heat pipe are in slidable contact with each other.

In alternative embodiments, the tubular member extends outwardly from the rotating cutting implement such that a longitudinal extending portion of the heat pipe is disposed within the tubular member. In a more particular embodiment, the tubular member is arranged so as to be a fixed member in which is disposed the rotating longitudinally extending portion of the heat pipe. As indicated herein, the tubular member can further include one or more or a plurality of reduced diameter regions disposed along a length of the tubular member, each of the reduced diameter regions being formed so as to at least reduce a gap between an inner surface of the tubular member and an outer surface of the longitudinally extending portion of the heat pipe.

In yet more particular embodiments, the surgical instrument further includes a shield member that is disposed and arranged so as to form a barrier between the rotating cutting element and collateral tissue about the surgical site (i.e., tissue that is not to be processed by the cutting element). In this way, damage to collateral tissue can be minimized such as if the end having the burr jumped or inadvertently moved during use. In more particular embodiments, such a shield member is secured to the fixed tubular member or shaft (e.g., distal end of the tubular member) to provide a fixed barrier to minimize the potential for damage to collateral tissue proximal the surgical end.

In yet further embodiments, such reduced diameter regions or contact regions extend circumferential about the tubular member, partially about the circumference or form a dimpled structure that extends along the length and/or about the circumference of the tubular member.

In alternative embodiments, the outer surface of the heat pipe is configured with surface artifacts that are formed so as to at least reduce a gap between an inner surface of the tubular member and an outer surface of the longitudinally extending portion of the heat pipe or formed so an inner surface of the tubular member and an outer surface of the longitudinally extending portion of the heat pipe are in slidable contact with each other.

In yet further embodiments, the heat pipe second end is arranged so as to be exposed to a cooling medium, whereby heat energy communicated to the heat pipe second end is dissipated to the cooling medium. Additionally, an outer surface of the heat pipe second end can include surface artifacts to facilitate transfer of heat energy from the heat pipe to the cooling medium. In further embodiments, such artifacts can comprise cooling fins.

In yet further embodiments, such surgical instruments, further include an active fluid cooling system that absorbs and removes heat energy by circulating a fluid and a portion of the heat pipe such as the heat pipe second end is thermally coupled to the active fluid cooling system to facilitate transfer of heat energy from the heat pipe to the circulating fluid.

In yet further embodiments, the tubular member is arranged so as to extend along the length of the heat pipe including the heat pipe second end and so as to be thermally coupled to the heat pipe second end whereby heat energy is dissipated from the heat pipe second end to the tubular member. In such embodiments, a tubular member portion proximal the heat pipe second end is arranged so as to be exposed to a cooling medium, whereby heat energy communicated to the heat pipe second end is dissipated by the tubular member to the cooling medium. Additionally, an outer surface of the tubular member can include surface artifacts (e.g., cooling fins) to facilitate transfer of heat energy from the tubular member to the cooling medium. In additional alternative embodiments, the tubular member portion can be thermally coupled to an active fluid cooling system to absorb and remove heat energy from the tubular member portion using a circulating fluid.

In yet further embodiments, the rotating cutting implement is a burr having a given shape. Also, such a burr can be utilized in connection with one of an ENT surgical procedure, an arthroscopy procedure and a laparoscopy procedure.

In yet further embodiments such a surgical instrument further includes one or both of a fluid delivery line and/or a suction line in proximity to the cutting implement so that the surgeon or user can introduce a fluid to the surgical site for clearing of debris resulting from the processing of the tissue using the surgical instrument. In addition, the introduction of a fluid also can be used as an additional means for cooling the tissue during use.

According to yet another aspect of the present invention, there is featured a motorized or powered surgical apparatus including a motor and a movable cutting assembly. In embodiments, the movable cutting assembly comprises any of the surgical instruments described herein including those instruments including embodiments described above. More particularly, such a movable cutting assembly includes a burr having a given shape and a heat pipe being arranged so as to absorb heat energy at one end thereof and dissipate the heat energy at least at a second end thereof. Also, the burr and heat pipe are arranged so that the heat pipe first end is thermally coupled to the burr so at least some heat energy being developed by the burr when in use is absorbed by the heat pipe first end and is communicated in the direction of the heat pipe second end. Also included is a tubular member that is connected to the burr and extends outwardly from the burr so that a longitudinal extending portion of the heat pipe is disposed within the tubular member. In addition, the tubular member is operably coupled to the motor such that when in use, the tubular member and the burr are rotated by the motor at a desired rotational speed.

In an alternative embodiment, the tubular member is a non-rotating fixed member in which is disposed the rotating longitudinally extending portion of the heat pipe. In this embodiment, the longitudinal extending portion of the heat pipe is operably coupled to the motor so the motor rotates the longitudinal extending portion of the heat pipe and the rotating cutting element (e.g., burr) that is connected thereto. Such a tubular member can further include one or more or a plurality of reduced diameter regions disposed along a length of the tubular member, each of the reduced diameter regions being formed so as to at least reduce a gap between an inner surface of the tubular member and an outer surface of the longitudinally extending portion of the heat pipe.

In yet further embodiments, the surgical instrument further includes a shield member that is disposed and arranged so as to form a barrier between the rotating cutting element and collateral tissue about the surgical site (i.e., tissue that is not to be processed by the cutting element). In this way, damage to the collateral tissue can be minimized such as if the end having the burr jumped or inadvertently moved during use. In more particular embodiments, such a shield member is secured to the fixed tubular member or shaft (e.g., distal end of the tubular member) to provide a fixed barrier to minimize the potential for damage to collateral tissue proximal the surgical end.

According to yet another aspect of the present invention, there are featured medical or surgical methods or procedures that employ the surgical instruments or apparatuses herein described. More particularly such methods include surgical or medical procedures for processing (e.g., cutting, grinding, abrading, debriding or the like) a feature (e.g., tissue, bone, ligaments and the like) of a mammalian body. More specifically, such methods or procedures which are intended for use for processing a feature of or associated with the ear, nose and/or throat (e.g., ENT procedure).

Such methods and procedures also include providing a surgical instrument or apparatus having a rotating cutting implement for use in processing a part of a mammalian body and a heat pipe that is arranged so as to absorb heat energy at one end thereof and to dissipate the heat energy at least at a second end thereof. In addition, the rotating cutting implement and heat pipe are arranged so that the heat pipe first end is thermally coupled to the rotating cutting implement so that at least some heat energy being developed by the rotating implement when in use is absorbed by the heat pipe first end and is communicated in the direction of the heat pipe second end.

Such methods and procedures of the present invention further include the step(s) of providing a surgical or medical instrument or a surgical or medical apparatus as herein described and processing a feature(s) of the mammalian body using such a surgical or medical instrument or a surgical or medical apparatus. In more particular embodiments such processing includes one of cutting, grinding, abrading, debriding or the like of the feature that includes for example, tissue, bone, ligaments and the like of a mammalian body. In further embodiments, such methods and procedures further include the step of absorbing heat energy from the cutting implement and dissipating the absorbed energy remote from the site where the body feature is being processed.

Other aspects and embodiments of the invention are discussed below.

DEFINITIONS

The instant invention is most clearly understood with reference to the following definitions:

As used herein the terms "cutting," "cut," "grinding" or "grind" when used in describing the methods, instruments or apparatus of the present invention shall be understood to be inclusive of any of a number of techniques or operations know in the art for surgically working or processing bone, cartilage or tissue such techniques include but are not limited to trimming, shaping, resecting, debriding, abrading or grinding of bone or tissue of a mammalian body.

The term tissue when used herein shall be understood to include other parts or structure of a human body including, but not limited to cartilage, muscle, bone, bony structures (e.g., vertebrae) and ligaments.

Endoscopy shall be understood to be generally referring to or describing a procedure which allows a doctor or surgeon to look inside a body (e.g., mammalian or human body) using an instrument called an endoscope for medical reasons. The doctor, surgeon or other medical personnel can use such a procedure for diagnostic purposes by examining or imaging the interior or exterior of an organ or cavity of the body and/or in combination with other surgical or diagnostic procedures (e.g., biopsy). For example, a cutting tool can be attached to the end of the endoscope or a tool can be provided for use in combination with the endoscope and the tool can then be used to perform surgery or biopsy. This type of surgery is generally called keyhole surgery as it usually leaves only a tiny external scar. Such endoscopic techniques have been developed and adapted for use in connection with specific parts or features of the human body and thus commonly have been given a specific name (e.g., colonoscopy).

Laparoscopic surgery is a surgical technique in which operations in the abdominal or pelvic cavities are performed through the use of small incisions and the use of a laparoscope in combination with a light source. The laparoscope is used to view the surgical site. The general term used to describe the process is laparoscopy.

Arthroscopy also referred to as arthroscopic surgery is another minimally invasive surgical procedure in which an examination and sometimes treatment of damage to the interior of a joint is performed using an arthroscope. An arthroscope is a type of endoscope that is inserted into the joint also through a small incision. Arthroscopic procedures are performed to evaluate and/or to treat many orthopedic conditions including floating cartilage, torn surface cartilage. ACL reconstruction and trimming of damaged cartilage.

ENT shall be understood to be generally referring to the ears, nose and throat of a mammalian body (e.g., human body) and ENT operations and procedures shall be understood to be describing and referring to operations and/or procedures involving the structure and features of such ears, nose and throat of the mammalian body.

Debridement, debriding or debride shall be understood to be describing the medical removal of dead, damaged or infected tissue to improve the healing potential of the remaining healthy tissue. Such removal is performed using any of a number of techniques known to those skilled in the art including surgical and mechanical. Surgical debridement is one of the fastest methods for debridement and is typically very selective as the surgeon or person performing the debridement has control over which tissue is being removed and which is being left behind.

USP shall be understood to mean U.S. Patent Number and U.S. Publication No. shall be understood to mean U.S. Published Patent Application Number.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 1 is a side view of a surgical instrument according to an aspect of the present invention.

FIG. 1A is a partial side view of a distal portion of the surgical instrument of FIG. 1, illustrating an embodiment thereof.

FIG. 1B is another partial side view of a distal portion of the surgical instrument of FIG. 1, illustrating another embodiment thereof.

FIG. 3A is a side view of a surgical instrument according to another aspect of the present invention including surface artifacts for cooling.

FIG. 3B is a partial side view of a distal portion of the surgical instrument of FIG. 3A, illustrating an embodiment thereof.

FIG. 3C is another partial side view of a distal portion of the surgical instrument of FIG. 3A, illustrating another embodiment thereof.

DESCRIPTION OF THE PREFERRED EMBODIMENT

Figure 2:
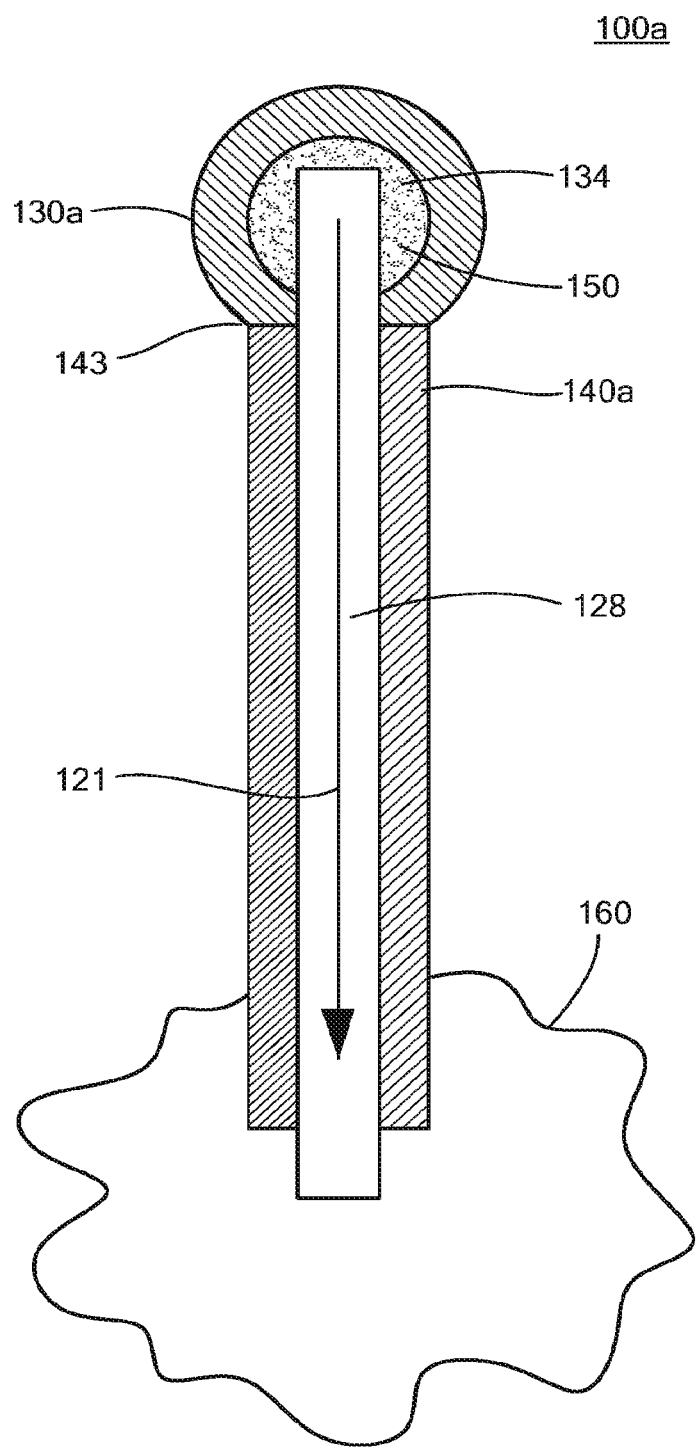
FIG. 2 is a cross-sectional side view of a surgical instrument similar to FIG. 1 but according to another embodiment of the present invention.

Referring now to the various figures of the drawing wherein like reference characters refer to like parts, there is shown in FIG. 1 a side view of a surgical instrument 100 according to an aspect of the present invention with partial cutaways. Referring also to FIG. 2, there is shown a cross-sectional side view of another surgical instrument 100a according to another embodiment of the present invention. The surgical instrument of FIG. 2 is similar to that of FIG. 1 and the like reference characters refer to like parts or common features. The differences there-between are discussed below.

The surgical instrument 100, 100a of either embodiment includes a heat pipe 120, and a cutting implement 130, 130a that is at least thermally coupled to the heat pipe and in more particular embodiments an end of the heat pipe and the cutting implement are mechanically coupled. In this regard the term distal as used herein in connection with the heat pipe and surgical instrument generally refers to a location that is in general proximity to the site in the body that is in contact with the cutting element and the term proximal is used to generally describe a location that is opposite the distal end and at an end opposite from proximity to this body site. As described further herein, the heat pipe 120 is rotated about its long axis during use so that the cutting implement 130, 130a can perform its intended function (e.g., cutting, abrading, grinding, debriding, etc.).

In further embodiments, portions of the heat pipe 120 is/are generally surrounded by an outer sleeve or shaft 140,140a that extends longitudinally about and along the length of the heat pipe. In illustrative exemplary embodiments, the shaft 140, 140a extends outwardly from the cutting implement 130, 130a to either a distal end of the heat pipe or to a point short of the distal end of the heat pipe as further described herein. In one embodiment, the shaft 140, 140a is secured to the cutting implement 130, 130a so that the shaft also is being rotated about the long axis of the heat pipe 120 during use. In an alternative embodiment and as illustrated and described in connection with FIGS. 5A-C, the shaft 140b-d is fixed with respect to the heat pipe 120 and the heat pipe rotates within the shaft. In more particular embodiments, the shaft 140, 140a is sized, configured and composed of a material that supports the heat pipe and more specifically provides compressive and flexural strength to the heat pipe. Such material includes a metal (e.g., steel) plastics or a composite material (e.g., graphite).

In further embodiments, an outer diameter 123 of the heat pipe 120 and an inner diameter 142 of the shaft 140,140a are established so as to minimize the space there-between and also to provide radial support to the heat pipe during rotation. In yet further embodiments and as more specifically illustrated in FIG. 1, an inner surface of the shaft inner diameter 142 includes surface artifacts 144 that extend outwardly from the outer surface so as to further reduce the space between an inner surface corresponding the shaft inner diameter 142 and a heat pipe outer surface corresponding to the heat pipe outer diameter 123. In more particular embodiments, the surface artifacts extend outwardly so as to be in contact (e.g., sliding or movable radial contact) with the heat pipe outer diameter. In this way, the shaft 140 can be slid longitudinally onto the heat pipe for purposes of assembly but allow the artifact(s) to be in contact with the heat pipe outer diameter for radial support as well as thermal conduction. In the case where the shaft is fixed, the artifacts also are such as to provide a mechanism whereby the heat pipe 120 can rotate about the longitudinal axis of the shaft.

Although two radially extending artifacts 144 extending from the shaft 140 are illustrated in FIG. 1, this shall not be limiting. It also is within the scope of the present invention for 2 or more, a plurality of, or a multiplicity of such radially extending artifacts 144 be provided in the inner surface of the shaft 144.

Alternatively, and with reference to FIG. 2, it is within the scope of the present invention for the shaft 140a to be configured so that the inner surface corresponding to the shaft inner diameter 142 is in sliding contact with the outer surface corresponding to heat pipe outer diameter 123 along the entire length of the shaft or portions thereof. In yet further embodiments, the shaft 140a is configurable so that that the inner surface corresponding to the shaft inner diameter 142 is spaced from the outer surface corresponding to heat pipe outer diameter 123 along the entire length of the shaft or portions thereof.

In addition, such artifacts can be formed so as to be disposed circumferentially about and along the length of the shaft so that the shaft is in arcuate contact with the heat pipe at the locations corresponding to such artifacts. Alternatively, the artifacts can be formed and arranged so as to form discrete regions along the length of the shaft that are in general point contact with the heat pipe (e.g., dimples). Also, the artifacts can be formed and arranged to create discrete, discontinuous arcuate regions (e.g., semicircular bands) about the shaft inner surface and along the length of the shaft. It also is within the scope of the present invention for these surface artifacts to be formed using any of a number of techniques known to those skilled in the art. For example, one or more or a plurality of regions of the shaft can be crimped radially so as to thereby form the radially extending artifacts.

Furthermore, while the artifacts are shown as extending from the shaft, this is not limiting as it also is within the scope of the present invention for the radially extending artifacts to be provided on the surface corresponding to the outer diameter of the heat pipe 120. For example, one or more bands of material (e.g., metals, plastics) can be secured to the surface of the heat pipe outer diameter such as with adhesives, brazing or welding (e.g., vibrational welding) to form the one or more surface artifacts.

The heat pipe 120 includes two ends, a distal end 122 and a proximal end 124 and a tubular member 126 interconnecting the two ends. As is known to those skilled in the art, the two ends 122, 124 and the tubular member 126 are connected or joined to each other so as to form a sealed structure. In either embodiment, the heat pipe distal end 122 is disposed within the cutting element 130, 130a (e.g., at the central core of the cutting element) to absorb heat energy and the proximal end 124 is where the absorbed heat energy is expected to be dissipated or dispersed.

As is known to those skilled in the art, a heat pipe is a phase change device that quickly equalizes thermal energy through phase change of liquids to vapor state within the heat pipe. In the present embodiment, the heat energy being absorbed at the distal end 122 changes the liquid phase to the vapor phase and the vapor phase is communicated to the proximal end 124 via the interconnecting tube 126 (i.e., direction of heat dissipation 121). The absorbed heat energy contained in the vapor phase is given up at the proximal end thereby causing the vapor phase to condense back into the liquid phase. The liquid phase is then communicated from the proximal end 124 to the distal end 122 via the interconnecting tube 126 so the above heat absorption and dissipation process can continuously repeat itself.

As is also known to those skilled in the art, the heat pipe 120 also is configurable with an internal wick structure 128, as more particularly illustrated in FIG. 2, such as a scintered metal or central wick structure. Such an internal wick structure 128 provides a mechanism by which the liquid phase can be communicated or transported more effectively to the proximal end, in particular when working against gravity. As is known to those skilled in the art, the distal and proximal ends 122, 124 and the interconnecting pipe 126 form a sealed structure and comprise any of a number of material known in the arts that are appropriate for the intended use. In an exemplary embodiment, the distal and proximal ends 122, 124 and the interconnecting pipe 126 are composed of a copper material or alloy.

In either embodiment, the heat pipe distal end 122 is disposed within the cutting element 130, 130a and so as to be at least in thermal contact with the cutting element. In more particular embodiments, the distal end 122 is firmly seated or secured within the cutting element 130, 130a. Referring now to the embodiment shown in FIG. 1, an aperture 132 is formed in the cutting element 130 in which the distal end is received. In more particular embodiments the outside surfaces of the distal end 122 becomes at least thermally engaged with the opposing surfaces of the aperture 132. In further embodiments, the outside surfaces of the distal end 122 become thermally and mechanically engaged with the opposing surfaces of the aperture 132 so as to secure the heat pipe distal end to the cutting element and so that the heat energy or thermal energy of friction is communicated to the distal end via the cutting element. In this way, the heat energy is absorbed by the liquid phase within the heat pipe 120 so as to thereby cause it to be converted to the vapor phase and then dissipated at the proximal end as described hereinabove.

Alternatively, and as shown in FIG. 2, in the other embodiment the cutting element 130a is formed or processed (e.g., machined) so as to have an interior cavity 134 that receives the distal end 122 of the heat pipe 120. The distal end 122 is secured and/or thermally coupled to interior surfaces of the cutting element 130 by a potting material 150 as is known to those skilled in the art. In particular embodiments, the potting material 150 is a thermal paste such as the silver thermal paste utilized for thermal coupling of personal computer functionalities (e.g., coupling of the processor on the motherboard to a heat dissipation device) or the like.

In further embodiments, the cutting element 130, 130a also is configured so as to facilitate conduction of thermal energy from friction during use of the medical instrument to the distal end 122 of the heat pipe. In exemplary embodiments, the cutting element 130, 130a is configured and arranged so that exterior walls of the cutting element 130, 130a are made as thin as possible consistent with needs of the cutting element to maintain structural integrity during use.

In addition, the interior cavity 134 of the cutting element is configurable so as to mirror or complement the overall shape of the cutting element. For example, if the cutting element 130, 130a forms an essentially spherical shape, then the interior cavity also can form a generally spherical interior cavity. While spherical shapes are illustrated, this is not limiting as the cutting element 130, 130a is configurable with any of a number of shapes known in the art including cylindrical, s-shaped and triangular and the interior cavity also is appropriately shaped including those shapes illustrated in FIGS. 5A-C. In addition, the heat pipe distal end 122 can be arranged so a portion thereof is in contact with a portion of the interior cavity 134 or can be spaced therefrom with the potting material interposed between the heat pipe and the walls of the interior cavity.

In yet further embodiments, the thermal conductivity capability of such a medical or surgical instrument is achievable using cutting elements that are particularly constructed to facilitate heat transfer alone as described herein, use of thermal potting materials such as a thermal paste to thermally couple the heat pipe and the cutting element alone and/or a combination of these two techniques.

In either surgical instrument embodiment, although more particularly illustrated in FIG. 2, the cutting element 130, 130a and the shaft 140, 140a (i.e., a support tube for the heat pipe) are configurable so that they are joined together using any of a number of mechanisms or techniques known to those skilled in the art (e.g., adhesives, welding, brazing and the like). For example, the heat pipe 120 and the cutting element 130, 130a, can be secured to each other as described herein using for example the thermal paste and then the shaft 140, 140a can be secured to the assembly of the heat pipe and cutting element by means of adhesives, welding and the like. The specific technique for joining is selected so as to be appropriate for joining the materials comprising the cutting element and the shaft. Also, for example, the cutting element and the shaft are further configured so as to form a joint 143 (e.g., welding joint or brazing joint) there-between that is appropriate for joining the two features. As indicated hereinafter, it also is within the scope of the present invention for the shaft to be arranged in fixed relation to the heat pipe and for the heat pipe to be rotatably disposed within the shaft.

In yet further embodiments, the cutting element 130, 130a and the shaft 140, 130a are composed of different materials (e.g., dissimilar metals) that are appropriate for the intended use. For example, the cutting element is composed of a material or combination of materials that are appropriate for cutting, grinding, abrading, debriding and the like and the shaft is composed of material having the appropriate strength characteristics or properties for supporting the heat pipe when under operating (e.g., rotational) conditions. In an exemplary embodiment, the cutting element is a burr made of tungsten carbide or stainless steel embedded with diamonds, the heat pipe is composed of a copper material and the shaft is composed of a steel such as stainless steel. In such a case, the burr is joined to the shaft using any of a number of techniques appropriate for joining the dissimilar materials and appropriate for the expected operational conditions (e.g., joining using adhesives or welding). The heat pipe also may include a coating such as silver on the outer surface or portions thereof to facilitate heat transfer such as between the cutting element and the heat pipe.

As indicated above, the heat energy absorbed at the heat pipe distal end 122 is dissipated at least at the heat pipe proximal end 124. As illustrated in FIGS. 1 and 2, according to an embodiment of the present invention, the heat pipe proximal end 124 extends outwardly from the shaft 140, 140*a* so that it is exposed to a heat sink 160 or cooling medium (e.g., atmosphere or a cooling source). In a particular embodiment, the heat pipe proximal end 124 extends fully beyond the shaft 140, 140*a* such that the heat energy communicated to the heat pipe proximal end is dissipated directly to the heat sink 160 or cooling medium.

Referring now to FIG. 1A, in another embodiment the shaft 140, 140*a* extends along the length of the heat pipe 120 such that the heat pipe proximal end 124 resides or is disposed within the shaft. In addition the shaft 140, 140*a* and the heat pipe proximal end 124 are configured and arranged so that they are thermally coupled to each other (e.g., by the artifacts 144 or the sliding contact). In this way, the heat energy is communicated to the shaft 140, 140*a* from the heat pipe proximal end 124 and thence from the shaft to the external heat sink 160 or cooling medium.

Referring now to FIG. 1B, in yet another embodiment, one part 124*a* of the heat pipe proximal end 124 is disposed within the shaft 140, 140*a* and the remaining part 124*b* of the distal end extends outwardly from the end of the shaft. In this way, heat energy can be dissipated through the shaft to the heat sink 160 and additionally, the heat energy can be dissipated from the exposed remaining portion 124*b* of the heat pipe proximal end.

Referring now to FIGS. 3A-C, there is shown a side view of a surgical instrument 100*c*1 according to another aspect of the present invention including surface artifacts for cooling (FIG. 3A); a partial side view of a distal portion of an embodiment of the surgical instrument 100*c*2 according to the another aspect (FIG. 3B) and another partial side view of a distal portion of another embodiment of a surgical instrument 100*c*3 according to the another aspect (FIG. 3C). In each of these embodiments, the surgical instrument 100*c*1-*c*3 is configured so the shaft 140, 140*a* and/or the heat pipe 120 is configured with surface artifacts 170, 170*a, b* that are thermally coupled to the respective shaft and/or heat pipe so that the heat energy absorbed at the heat pipe proximal end 124 is dissipated to the heat sink 160. In a particular embodiment, each surface artifact 170 comprises an outwardly extending member as are known in the art, such as a blade, fin or pin like structure, from which heat can be dissipated to the heat sink 160.

Referring now to FIG. 3A, the heat pipe proximal end 124 extends outwardly from the shaft 140, 140*a* so that it is exposed to the heat sink 160 or cooling medium (e.g., atmosphere or a cooling source). In a particular illustrative embodiment, the heat pipe proximal end 124 extends fully outwardly from the shaft 140, 140*a*.

In addition, one or more surface artifacts 170 are arranged on an outer surface of the heat pipe proximal end 124 and are thermally coupled to the outer surface of the proximal end. In particular embodiments one of a plurality of surface artifacts 170, a multiplicity of surface artifacts, three or more surface artifacts, or four or more surface artifacts are thermally coupled to and arranged on and about the outer surface of the heat pipe proximal end 124. In particular embodiments, each surface artifact 170 comprises an outwardly extending member as are known in the art, such as a blade, fin or pin like structure, from which heat can be dissipated. In this way, heat energy communicated to the heat pipe proximal end 124 is dissipated through the surface artifacts alone or in combination with the outer surface of the heat pipe proximal end to the heat sink 160 or cooling medium.

Referring now to FIG. 3B, in another embodiment the shaft 140, 140*a* extends along the length of the heat pipe 120 such that the heat pipe proximal end 124 resides or is disposed within the shaft. In addition, the shaft 140, 140*a* and the heat pipe proximal end 124 are configured and arranged so that they are thermally coupled to each other (e.g., by the artifacts 144 or the sliding contact). In this way, the heat energy is communicated to the shaft 140, 140*a* from the heat pipe proximal end 124.

In addition, one or more surface artifacts 170 are arranged on an outer surface of the shaft 140, 140*a* and are thermally coupled to the outer surface thereof. In particular embodiments one of a plurality of surface artifacts 170, a multiplicity of surface artifacts, three or more surface artifacts, or four or more surface artifacts are thermally coupled to and arranged on and about the outer surface of the shaft 140, 140*a*. In particular embodiments, each surface artifact 170 comprises an outwardly extending member as are known in the art, such as a blade, fin or pin like structure, from which heat can be dissipated. In this way, the heat energy being communicated to the shaft 140, 140*a* is dissipated through the surface artifacts alone or in combination with the outer surface of the shaft to the heat sink 160 or cooling medium.

Referring now to FIG. 3C, in yet another embodiment, one part 124*a* of the heat pipe proximal end 124 is disposed within the shaft 140, 140*a* and the remaining part 124*b* of the proximal end extends outwardly from the end of the shaft. In this way, heat energy to be dissipated is communicated to the shaft 140, 140*a* and additionally, the heat energy is communicated to the exposed remaining portion 124*b* of the heat pipe proximal end 124.

In addition, one or more surface artifacts 170*a* are arranged on an outer surface of the shaft 140, 140*a* and are thermally coupled to the outer surface thereof and one or more surface artifacts 170*b* also are arranged on an outer surface of the heat pipe proximal end 124 and are thermally coupled to the outer surface of the proximal end. In particular embodiments one of a plurality of surface artifacts 170*a, b*; a multiplicity of surface artifacts, three or more surface artifacts, or four or more surface artifacts are thermally coupled to and arranged on and about the outer surfaces of the heat pipe proximal end 124 and/or the shaft. In particular embodiments, each surface artifact 170 comprises an outwardly extending member as are known in the art, such as a blade, fin or pin like structure, from which heat can be dissipated. In this way, heat energy communicated to the heat pipe proximal end 124 is dissipated through the surface artifacts 170*a, b* alone or in combination with the outer surface of the respective shaft and/or proximal end to the heat sink 160 or cooling medium.

Figure 4:
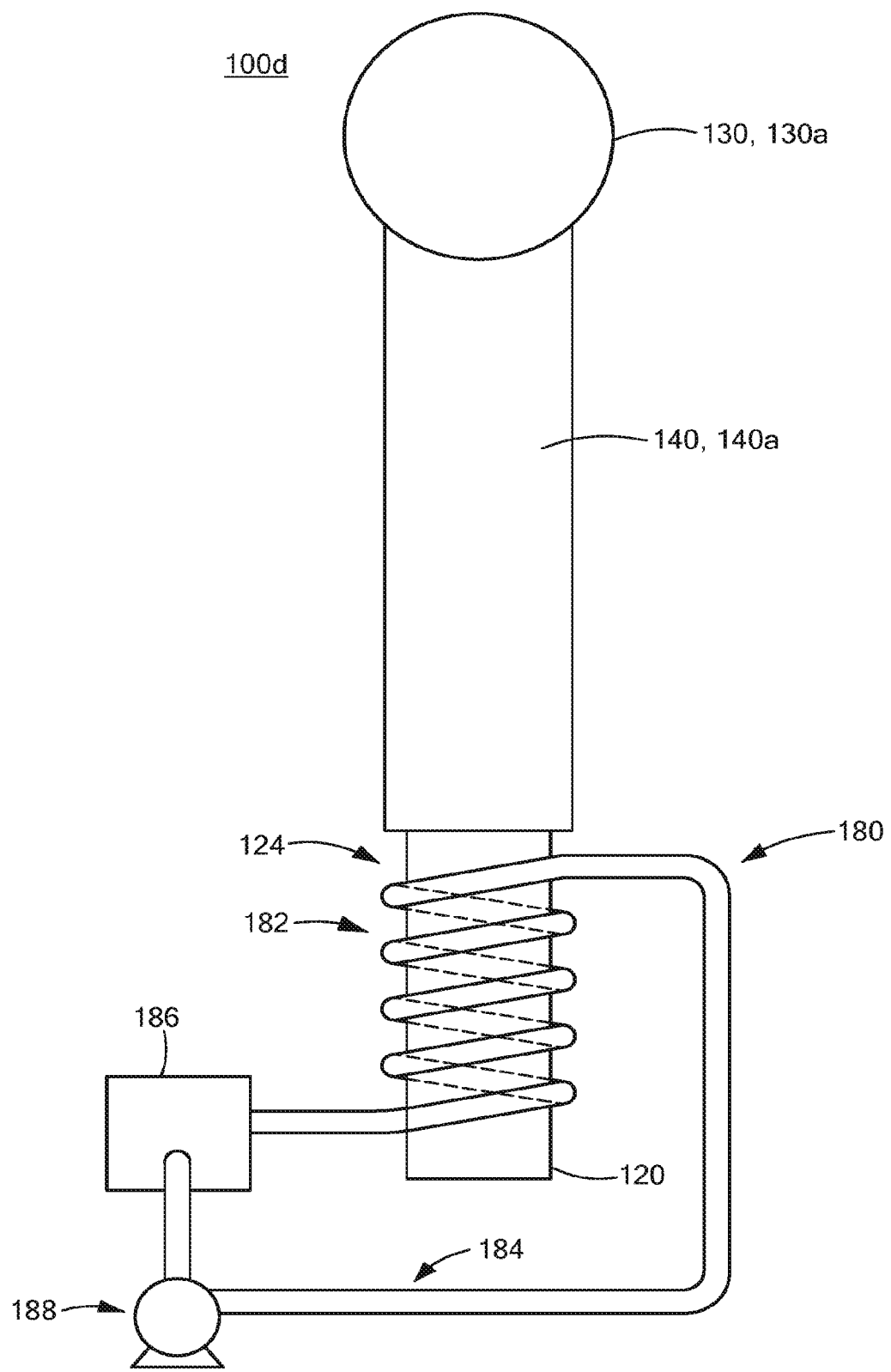
FIG. 4 is an illustrative view of a surgical instrument according to yet another aspect of the present invention in which the heat pipe is at least thermally coupled to an external cooling system.

Referring now to FIG. 4, there is shown an illustrative view of a surgical instrument 100*d* according to yet another aspect of the present invention further comprising an external active cooling system 180 that is thermally coupled to the proximal end 124 of the heat pipe 120 so that heat energy being communicated to the proximal end is dissipated in the cooling system. It should be recognized that the present invention is not limited to the illustrated embodiment. It is within the scope of the present invention for such an external cooling system 180 to be configured and adapted so that it is thermally coupled to the shaft 140, 140a (e.g., outer surface thereof) by, for example, wrapping a cooling coil 182 about the shaft proximal the heat pipe proximal end. Alternatively, similar to that shown in FIG. 3C, one or more cooling coils are configurable so as to be thermally coupled to the outer surface of the shaft 140, 140a proximal one portion 124a of the heat pipe proximal end and the outer surface of the remaining portion 124b of the proximal end 124.

In such an active fluid cooling system 180, the heat energy absorbed by the heat pipe 120 is absorbed and removed by a fluid, more particularly a flowing fluid. In particular embodiments, such heat energy is absorbed by a fluid flowing through the cooling coil 182. Also, this absorbed heat energy is then removed using any of a number of techniques known to those skilled in the art. In one exemplary embodiment, the system 180 is configurable so that an inlet of the cooling coil 182 is connected to a fluid source, such as the source of water used for irrigation and the outlet is connected to a suction source such as the suction source used for suctioning the irrigated water or to a fluid drain into which the heated cooling fluid can be dispersed. In this way, the system 180 utilizes functionalities that are generally available and which functionalities would be used in surgical procedures along with the surgical instruments of the present invention.

In another illustrative exemplary embodiment, the process is controlled so that the fluid makes one or more passes through the cooling coil 182 and then to a fluid receiving apparatus 186 in the form of, for example, a large tank or a heat exchange device. The fluid having the absorbed heat energy is dispersed in the large tank or cooled by the heat exchange device. The fluid from the tank or heat exchange device is returned to the cooling coil such as, for example, by a pumping mechanism 188 (e.g., any of a number of pumps known in the art and appropriate for the intended use) via a pipe 184 or conduit. In the case of the large tank, the volume of fluid in the tank is typically such that the mixing of the heated fluid with the fluid in the tank does not significantly alter the temperature of the tank fluid during the use of the surgical instrument. As heat exchangers or heat exchange devices and the process for dissipating heat energy using such heat exchangers or heat exchange device are well known in the art, the related heat exchange process is not further described herein.

Figure 5A:
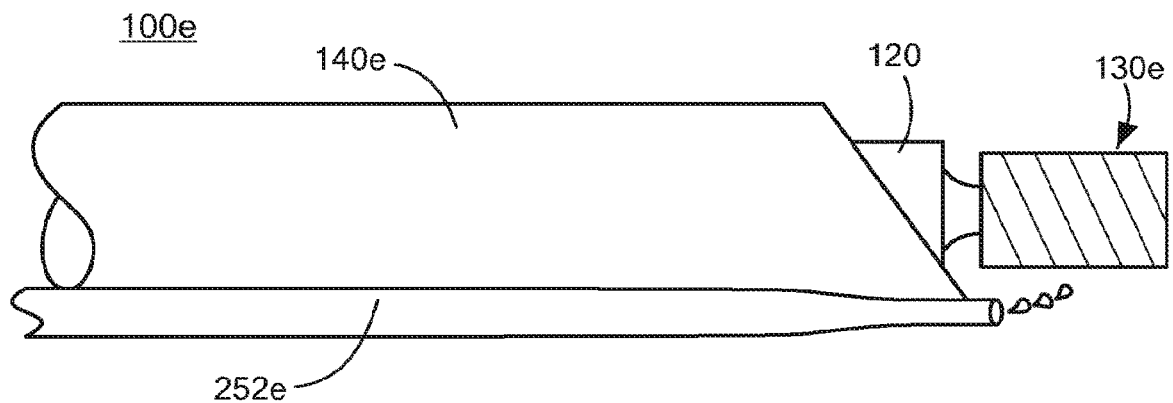
FIG. 5A is an illustrative view of a distal portion of a surgical instrument according to another aspect of the present invention including a fluid line.
Figure 5B:
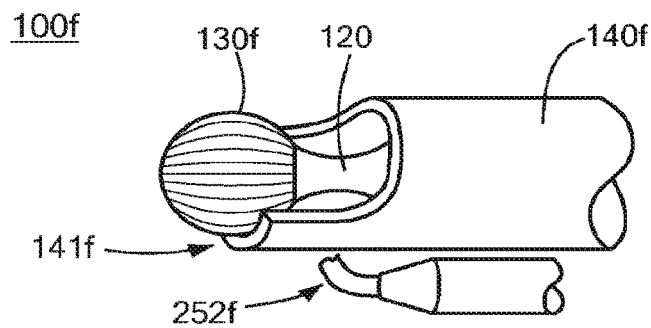
FIG. 5B is another illustrative view of a distal portion of a surgical instrument according to another aspect of the present invention including a shield or barrier and a fluid line.
Figure 5C:
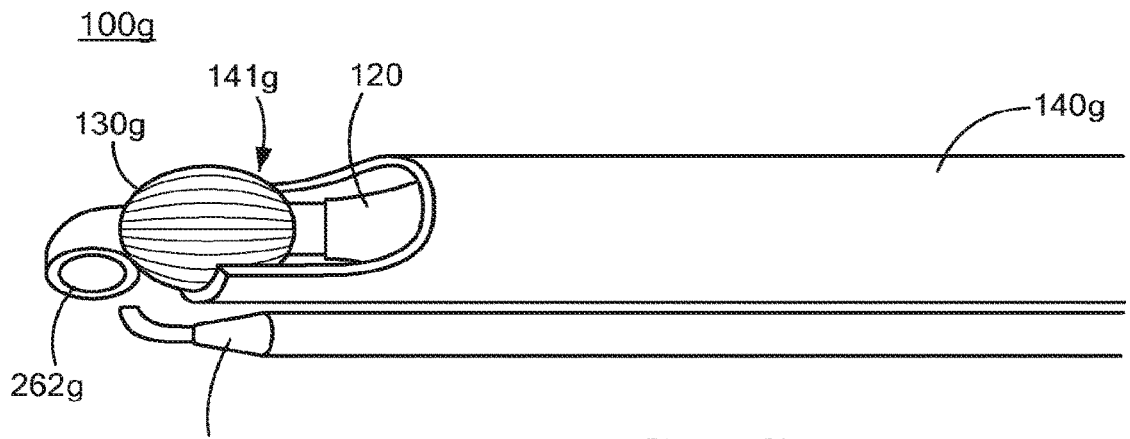
FIG. 5C is another illustrative view of a distal portion of a surgical instrument according to another aspect of the present invention including a shield or barrier, a fluid line and suction line.

Referring now to FIGS. 5A-C there are shown surgical instruments 100e-g according to yet another aspect of the present invention. In each of the illustrated embodiments, the tubular member 140e-g or shaft is fixed and the heat pipe 120 is rotationally disposed and supported within the tubular member. In an exemplary embodiment, the tubular member 140e-g is coupled to external structure such as the handle 210 (FIG. 6-7) of a powered surgical or medical apparatus 200. In a further embodiment, the tubular member 140e-g is removably coupled to such external structure using any of a number of techniques known to those skilled in the art.

As indicated, the heat pipe 120 is rotationally disposed and supported within the tubular member 140e-g. In this regard, the artifacts 144 described hereinabove, can be further adapted so as to provide the appropriate rotational support for the heat pipe 120 while it is rotating during operation. Such rotational support artifacts can be provided on the heat pipe and/or the tubular member. In addition, such rotational support artifacts can comprise any of a number of structures (e.g., ball bearing based structures, Teflon coated surfaces) that are otherwise appropriate for the intended use.

Referring now to FIG. 5A, there is shown an illustrative view of a distal portion of a surgical instrument 100e according to another aspect of the present invention including a fluid line 252e being connected to a source 250 (FIG. 6) of fluid. In the illustrated embodiment, the fluid line 252e is coupled to the tubular member 140e and extends along the length of the tubular member at least in the area in proximity to the distal end of the tubular member. Also, the fluid flows outwardly from the open end of the fluid line so as to generally spray onto the cutting implement 130e and onto the tissue being processed by the cutting implement and tissue proximal the surgical site (e.g., collateral tissue).

In that illustrated embodiment, at least the cutting implement 130e extends from the distal end of the tubular member 140e. In more particular embodiments, a portion of the distal end of the heat pipe 120 also extends from the tubular member distal end. As indicated herein, the cutting element 130e can have any of a number of shapes known in the art, including the illustrated cylindrical shape and a spherical shape as more particularly shown in FIG. 5B.

Referring now to FIG. 5B there is shown an illustrative view of a distal portion of another embodiment of a surgical instrument 100f according to the "another" aspect of the present invention. Such a surgical instrument includes, inter alia, a shield 141f or barrier and a fluid line 252f that is connected to a source 250 (FIG. 6) of fluid. A portion of the tubular member 140f is arranged so it extends outwardly so as to form the shield 141f or barrier (e.g., an arcuate shield or barrier) about a portion of the cutting implement 130f. This shield or barrier preferably is arranged such that during use the shield is between the cutting implement and tissue adjacent to the surgical site. In this way, an inadvertent motion of the cutting implement should not contact and damage this adjacent tissue. In an alternative embodiment, the shield 141f or barrier is a separate element that is secured to the distal end of the tubular member such that it extends outwardly from the tubular member to shield the adjacent tissue from the cutting element.

In this embodiment, a portion of the cutting implement 130f extends beyond the shield 141f and extends outwardly from the open distal end of the tubular member 140f. In more particular embodiments, a portion of the distal end of the heat pipe 120 also extends from the open end of the tubular member. As indicated herein, the cutting element 130f can have any of a number of shapes known in the art, including the oval shape as more particularly shown in FIG. 5C.

In the illustrated embodiment, the fluid line 252f is coupled to the tubular member 140f and extends along the length of the tubular member at least in the area in proximity to the distal end of the tubular member. In more particular embodiments, the fluid line also embodies a constricting element (e.g., reducer) to increase flow velocity and a redirection element (e.g., elbow) so as to redirect the fluid flow to a given direction. In the illustrated embodiment, the fluid flow is re-directed so as to more particularly impinge on the cutting element 130f and the shield 141f. In addition, the fluid also flows so as to generally spray onto the tissue being processed by the cutting implement and the tissue proximal the surgical site (e.g., collateral tissue).

Referring now to FIG. 5C, there is shown another illustrative view of a distal portion of another embodiment of a surgical instrument 100g according to the "another" aspect of the present invention. Such a surgical instrument includes, inter alia, a shield 141g or barrier, a fluid line 252g and suction line 262g. The fluid line 252g is connected to a source 250 (FIG. 6) of fluid and the suction line is connected to a suction source 260 (FIG. 6).

In the illustrated embodiment, a portion of the tubular member 140g is arranged so it extends outwardly so as to form the shield 141g or barrier (e.g., an arcuate shield or barrier) about a portion of the cutting implement 130g. Reference shall be made to the discussion of FIG. 5B for the corresponding features as to further details of the fluid line 252g, the shield 141g, the tubular member 140g and cutting element 130g of this embodiment. As indicated herein, the shield can be a separate member that is coupled or attached to the distal end of the tubular member. As also indicated herein, the shield or barrier is preferably arranged so that during use the shield is positioned between the cutting implement and tissue adjacent to the surgical site. In this way, an inadvertent motion of the cutting implement should not contact and damage the adjacent tissue.

In the illustrated embodiment, the suction line 262g is coupled to the tubular member 140g and extends along the length of the tubular member at least in the area in proximity to the distal end of the tubular member. Preferably, the open end of the suction line 262g also is positioned so as to be downstream of the cutting element 130g and fluid line 252g so the suction line removes or suctions fluid and/or debris from the processing of the tissue by the cutting element. This preferably also includes suctioning the fluid that was sprayed onto the tissue being processed by the cutting implement and tissue proximal the surgical site (e.g., collateral tissue).

Figure 6:
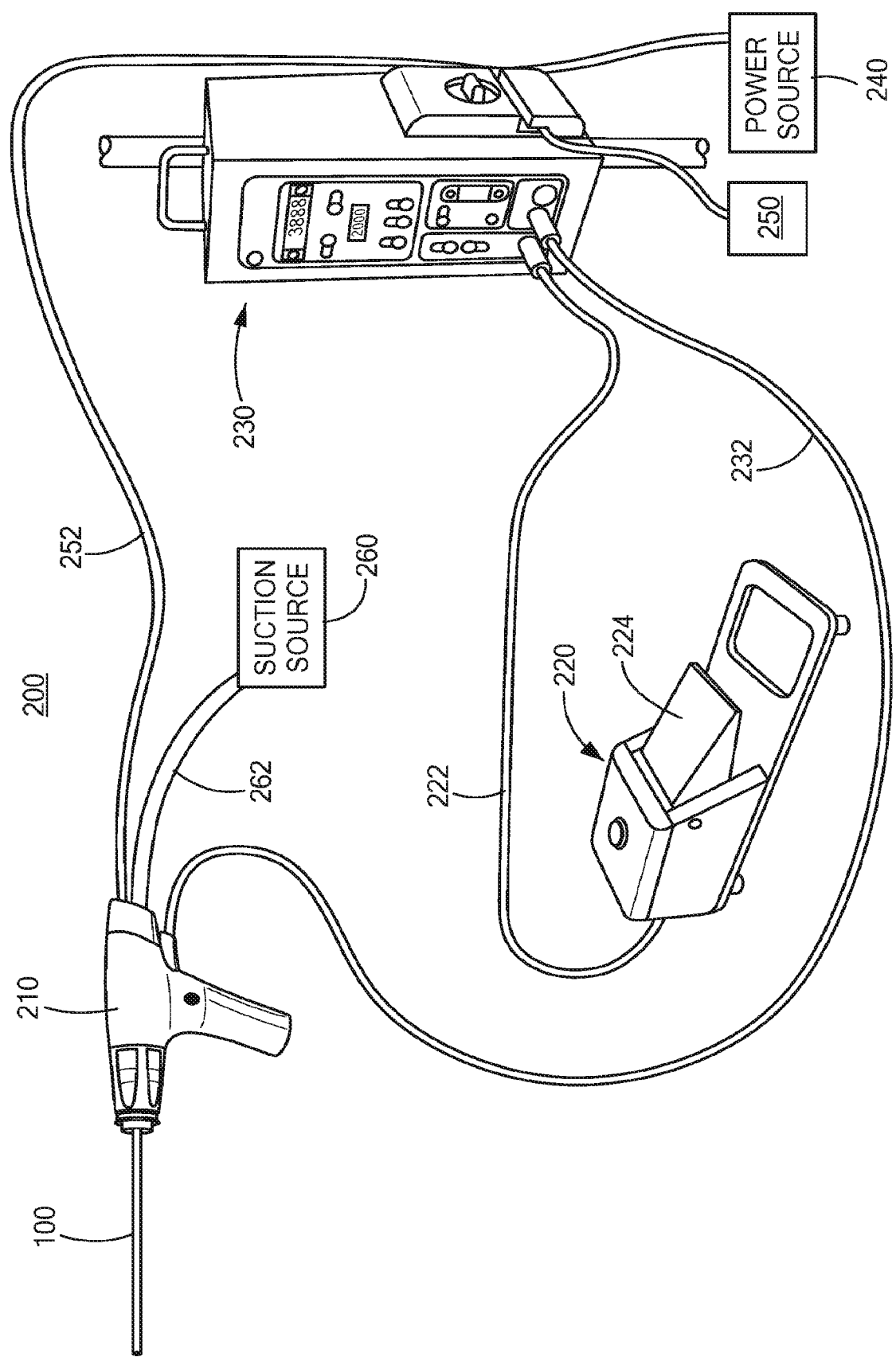
FIG. 6 is a schematic view of an exemplary powered surgical apparatus according to the present invention.
Figure 7:
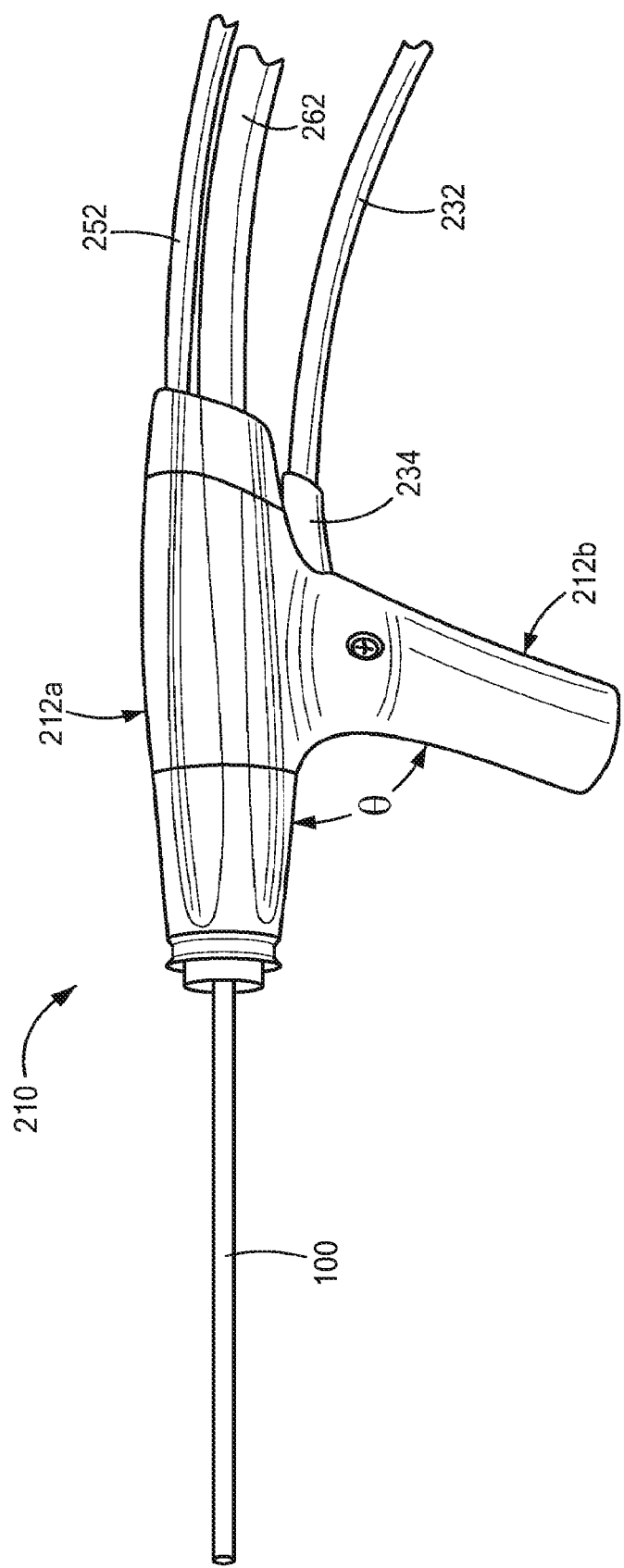
FIG. 7 is a perspective exterior view of the handle shown in FIG. 6.

Referring now to FIGS. 6-7 there is shown a schematic view of an exemplary powered surgical or medical apparatus 200 according to the present invention (FIG. 6) and a perspective exterior view of the handle 210 shown in FIG. 7. Such a surgical or medical apparatus 200 is easily adaptable for use with any of a number of surgical instruments as are known to those skilled in the art as well as the above described surgical instruments of the present invention. Reference shall be made to U.S. Pat. No. 7,247,161 the teachings of which are incorporated herein by reference, for further details as to the powered surgical apparatus or powered medical apparatus not otherwise described herein. It shall be recognized, however, that the surgical instrument(s) of the present invention is/are adaptable for use in combination with any of a number of powered surgical apparatus as are known to those skilled in the art that include a cutting implement or device that is operably coupled to a power source to rotate the surgical instrument. In the discussion concerning FIGS. 6-7 the surgical or medical instrument is identified by reference numeral 100, for simplifying the discussion. This, however, shall be not considered as limiting the described apparatus 200 to use with only this particular medical instrument as it is within the scope of the present invention for such an apparatus to be used with any of the herein described or illustrated surgical instruments.

Also, the medical or surgical instruments of the present invention are particularly advantageous as the heat pipe allows the removal of the heat of friction from the proximal end to the distal end without the need for an external source of fluid (e.g., water) for cooling and suction to remove the heated fluid directly from the surgical site. In addition, such a surgical instrument or cutting blade assembly of the present invention also advantageously provides a structure that does not require the source of irrigation fluid and/or the suction source to directly be connected to it, which enables the surgical instrument 100 to be changed out during a surgical or medical procedure without requiring that the source of irrigation fluid and/or the suction source to be disconnected from the handle 210 of the apparatus 200.

The exemplary powered surgical or medical apparatus 200 includes a handle 210, a footswitch 220 and a controller 230. A general description of these elements as well as their interrelationship is provided below.

The surgical instrument 100 is removable and operably coupled to the handle 210 which includes a motor assembly for driving the surgical instrument for purposes of cutting, shaving, grinding, abrading or otherwise removing bodily material in accordance with a surgical, diagnostic or medical procedure or technique. Such removable and operable coupling shall include any of a number of techniques known to those skilled in the art that are appropriate for rotating the surgical instrument 100 that extends outwardly from the handle or other surgical apparatus to which the medical instrument is mounted to.

Such a handle 210 also is configurable so the proximal end 124 of the heat pipe 120 (FIG. 1) is appropriately thermally coupled to the external heat sink. In an illustrative embodiment, the handle 210 is thermally coupled to the shaft 140 or support member so that the heat energy being absorbed from the heat pipe distal end 122 is communicated to the handle 210 (e.g., directly or via the shaft 140) and thence to the surrounding atmosphere.

In another embodiment, the handle 210 is configured so as to include one or more openings or ports that are arranged proximal the heat pipe proximal end 124 when the surgical instrument is operably disposed within the handle. In this way, the absorbed heat energy is dispersed from the heat pipe and/or the shaft 140 via these openings.

As indicated above in connection with the discussion regarding FIGS. 3A-C, the heat pipe and/or the shaft are configurable so as to include one or more surface artifacts 170 to facilitate the transfer of the absorbed heat energy to the atmosphere. In such further embodiments, the handle and openings therein are further configured so as to provide a space between the structure of the handle and the rotating surface artifacts.

As indicated above in connection with the discussion regarding FIG. 4, an active cooling system 180 is provided that is thermally coupled to the heat pipe proximal end 124 directly and/or via the portion of the shaft 140 about the heat pipe proximal end. In such a system, a cooling fluid passes through a cooling coil 182, which in turn absorbs the heat energy being dissipated from the heat pipe proximal end. In this embodiment, the handle 210 also is configured so as to receive the structure of the cooling coil and the associated inlet and outlet lines. In further embodiments, the handle 210 can further include fluid lines fluidly coupling these inlet and outlet lines respectively to the irrigation source 250 and the suction source 260.

The medical instrument 100 or other cutting blade assembly as is known to those skilled in the art is arranged so as to extend from the distal end of the handle 210. As described herein, the distal end of the medical instrument 100 or cutting blade assembly is usable to cut, shave, grind, abrade and/or remove bodily material during a surgical procedure or operation. The distal end of the medical instrument 100 or cutting blade assembly can perform the cutting, shaving and/or removal in any manner, such as by rotation, for example. In operation, a surgeon grasps the handle 210 as if grasping a pistol and brings the distal end of the surgical instrument or cutting blade assembly into contact with the bodily material to be shaved, cut and/or removed.

The footswitch 220 is operably connected to the controller 230, for example, via a footswitch signal line 222, such as an electric cable. The footswitch 220 is typically disposed on the floor of a surgical room within reach of the surgeon's foot. The footswitch 220 includes an actuator member, such as a foot pedal 224, the actuation of which results in an input signal being transmitted to the controller 230 via the footswitch signal line 222. In operation, the surgeon places his or her foot on the footswitch 222 and depresses the foot pedal 224 to provide an input signal to the controller for the purpose of controlling at least one operation of the apparatus, such as energizing/de-energizing rotation of the medical instrument 100 or cutting blade assembly, or speed of rotation of the medical instrument 100 or cutting blade assembly, for example. However, the footswitch signal line can be used for any other purpose, such as to transmit other types of signals to the controller 230, to transmit signals from the controller 230 to the footswitch, or to supply power to the footswitch, for example.

Alternatively, or additionally, the handle can include a trigger switch assembly as are known to those skilled in the art and used in lieu of, or in addition to, the footswitch 220. The trigger switch assembly can be actuatable such that, while the surgeon grasps the handle as if grasping a pistol, one or more of the surgeon's fingers can press a part of the trigger switch assembly toward the handle as if pulling the trigger of the pistol (e.g., depressing the trigger such as done with a conventional drill).

The controller 230 also is operably connected to the handle 210 via a handle signal line 232. In this way, the controller 230 can output signals to the handle via the handle signal line, for example, control signals controlling on/off status of the surgical instrument 100 or cutting blade assembly, and/or rotation speed of the medical instrument 100 or cutting blade assembly (e.g., based upon input signals received by the controller 230 from the footswitch). The handle signal line, however, is useable for any of a number of other purposes, such as to transmit other types of signals to the handle 210, to transmit signals from the handle 210 to the controller 230, or to supply power to the handle, for example. For example, the handle supply line also is useable to transmit signals to the controller 230 indicating the type of handle 210 that is currently connected to the controller.

In the illustrative embodiment, the controller 230 is also connected to a power source 240 via a power source supply line, such as a standard electric cable or hospital grade power cord, for example. The controller receives and utilizes a source of AC or DC electric voltage from the power source or it also can receive and utilize a source of DC electric voltage.

The handle 210 or hand piece can be connected to a source 250 of irrigation fluid by an irrigation fluid supply tube 252. The irrigation fluid can be provided so as to pass through the handle 210 to the surgical site for the purpose of lubricating the blade or blades for enhanced cutting or shaving efficiency, for example. The irrigation fluid can be provided for any other purpose, such as flushing out the surgical site for enhanced removal of cut or shaven bodily material, for example.

As described herein, the medical instrument 100d according to an embodiment of the present invention is coupled to an active fluid cooling system 180 where the irrigation fluid source 250 is fluidly coupled to the coiling cool 182 of such a system. In this embodiment, a fluid branch can be provided to fluidly couple the cooling coil 182 to the irrigation line 252. In such an active fluid cooling system embodiment, the heat energy absorbed by the heat pipe 120 is absorbed and removed by the irrigation fluid flowing through the cooling coil 182. Additionally, this absorbed heat energy is then removed, for example, by fluidly coupling the outlet of the cooling coil 182 to a suction source such as the suction source 260 used for suctioning the irrigated water.

The irrigation fluid is supplied from the irrigation fluid source 250 to the handle 210 or surgical site using by any or a number of techniques and/or mechanisms known to those skilled in the art.

In the illustrative embodiment, the handle 210 is fluidly connected or coupled to a source of suction 260 by a suction supply tube 262. The suction can be provided so as to extend through the handle and thence to the surgical site for the purpose or removing cut or shaven bodily material and/or irrigation fluid. However, as indicated above, the suction can be provided for any other purpose such as being fluidly coupled to the outlet of the cooling coil 182.

The above overall system description of the apparatus 200 is provided for exemplary purposes only. The invention is not only intended to cover the above described overall system, but also various other aspects of the individual elements or combinations of the individual elements of the overall system. Thus, any of the other aspects of the individual elements of the invention can be utilized individually, with combinations of the above individual elements or in conjunction with systems that are quite different than the overall system discussed above and still be within the spirit and scope of the invention.

The handle 210 includes an upper portion 212a and a lower portion 212b that define a pistol grip. The operator, such as a surgeon, grasps the handle 210 as if gripping a pistol, a drill or the like. The specific manner of grasping the handle is determined by the operator's preference. In an exemplary method of grasping the handle, the surgeon's palm is pressed against a rear end of the lower portion 212b, while one or more of the surgeon's fingers can wrap around a front end of the lower portion. One or more of the surgeon's fingers also can extend along the upper portion 212a. Such a pistol grip can provide an ergonomic advantages, e.g., the operator may find the pistol grip easier to hold for long periods of time, easier to operate with one hand or easier to precisely manipulate the surgical instrument 100 or cutting blade assembly to its desired target area.

The handle signal line 232 is connected to the handle via a cable assembly 234, which is then electrically connected to a motor assembly. The controller 230 can thereby send control signals to the motor assembly via the handle signal line and cable assembly to actuate the motor on and off and to regulate the speed of the motor. However, the controller 230 can send and/or receive any other signals to or from the motor assembly via the handle signal line 232 and cable assembly 234.

In yet further aspects, the present invention features surgical, diagnostic and medical methods that embody such medical instruments 100 and/or apparatus 200. In the within discussion, the surgical or medical instrument is identified by reference numeral 100, and the apparatus is identified by reference numeral 200 for simplifying the discussion. This, however, shall not be considered as limiting the methods of the present invention to the identified apparatus or surgical instrument. It is within the scope of the present invention for such methods to use any of the herein described or illustrated apparatus or surgical instruments.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A surgical instrument comprising:
    an end effector;
    a cooling device, thermally coupled to the end effector and configured to absorb heat energy from the end effector, wherein the cooling device includes a phase change device including a heat pipe including a sealed internal cavity providing evaporation and condensation of a phase change medium within the sealed internal cavity; and wherein the end effector includes a rotatable cutting element including a cavity that is configured and arranged to receive the first end of the heat pipe.

2. The surgical instrument of claim 1, wherein the heat pipe includes a first end and a second end, and wherein the heat pipe is configured to absorb heat energy at the first end, to transfer the heat energy, and to dissipate the heat energy at least at the second end.

3. The surgical instrument of claim 2, wherein the second end of the heat pipe is arranged so as to be exposed to a cooling medium, wherein at least a portion of the heat energy transferred to the second end of the heat pipe is dissipated to the cooling medium.

4. The surgical instrument of claim 1, wherein the heat pipe further includes a material disposed in the interior of the heat pipe to facilitate movement of the phase change medium along a length of the heat pipe.

5. The surgical instrument of claim 1, wherein the end effector includes a cutting implement.

6. The surgical instrument of claim 5, wherein the cutting implement includes a rotating cutting implement.

7. The surgical instrument of claim 1, further comprising a tubular member that is connected to the end effector and that extends outwardly from the end effector such that a longitudinal extending portion of the heat pipe is disposed within the tubular member.

8. The surgical instrument of claim 7, wherein the tubular member further includes a plurality of contact regions disposed along a length of the tubular member, each of the plurality of contact regions being formed so that an inner surface of the tubular member and an outer surface of the heat pipe are in slidable contact with each other.

9. A method of using an end effector, the method comprising:
    introducing the end effector into a body;
    absorbing heat energy from the end effector by a cooling device, wherein the cooling device includes a phase change device including a heat pipe including a sealed internal cavity providing evaporation and condensation of a phase change medium within the sealed internal cavity, wherein the end effector includes a rotatable cutting element including a cavity that is configured and arranged to receive the first end of the heat pipe.

10. The method of claim 9, wherein the heat pipe includes a first end and a second end, and wherein the heat pipe is configured to absorb heat energy at the first end, and to transfer at least a portion of the heat energy to the second end, and to dissipate at least a portion of the heat energy at least at the second end.

* * * * *